United States Patent [19]

Weinberger

[11] Patent Number: Plant 5,503

[45] Date of Patent: Jul. 2, 1985

[54] PEACH TREE, "SUPECHFOUR"

[75] Inventor: John H. Weinberger, Fresno, Calif.

[73] Assignee: Superior Farming Company, Bakersfield, Calif.

[21] Appl. No.: 555,017

[22] Filed: Nov. 25, 1983

[51] Int. Cl.[3] ..... A01H 5/00

[52] U.S. Cl. ..... Plt./43

[58] Field of Search ..... Plt./43

*Primary Examiner*—James R. Feyrer

*Attorney, Agent, or Firm*—Huebner & Worrel

[57] ABSTRACT

A peach tree generally similar to the Flavorcrest Peach Tree (unpatented) which bears large, smooth, nearly globular fruit having a more highly-colored skin than that of the Flavorcrest and ripening about three days earlier than the Flavorcrest.

1 Drawing Figure

BACKGROUND OF THE NEW VARIETY

The present invention relates to a new and distinct variety of peach tree which has been assigned the varietal name "Supechfour" and which is generally similar to the Flavorcrest Peach Tree (unpatented), but which bears fruit which is more highly colored and which ripens about 3 days earlier than that of Flavorcrest.

The Flavorcrest Peach Tree is well known as producing large, round fruit having a bright red skin with a bright yellow ground color and further having yellow, firm flesh of smooth texture and very good flavor. Such a combination of qualities in a peach tree has long been recognized as desirable in the development of a peach tree bearing fruit which will gain commercial acceptance. To a large extent, fresh market consumer selection of a given peach variety is greatly influenced by the degree to which the skin of the fruit is vividly colored. Thus, it has long been known that a highly-colored skin has the potential to add to a fruit's marketability.

From a competitive standpoint, it is well recognized that a peach variety generally resembling a previously successful peach variety will stand a greater chance of competing in the open market if that fruit can be brought to market at a time other than that at which the accepted variety is sold. Thus, it has long been recognized that it would be desirable to have a peach variety generally similar to the Flavorcrest variety but which produces fruit which is more highly colored and which ripens at an earlier date.

ORIGIN AND ASEXUAL REPRODUCTION OF THE NEW VARIETY

The new variety of peach tree was discovered by me growing as a seedling hybrid of a cross between a Flavorcrest Peach Tree (unpatented) and a Springcrest Peach Tree (unpatented), the seedling having been planted as part of a planned breeding program conducted by me on behalf of Superior Farming Company of Bakersfield, Calif., a California Corporation. Such breeding took place in 1975 and was personally conducted by me, or by my assistants under my direction, supervision and control, on land owned by Superior Farming Company and located at 5090 East Church Avenue, Fresno, Calif.

The seedling was grown to fruiting and in 1978 I observed the new and distinct characteristics of the new variety. I asexually reproduced the new variety by inserting buds from the variety into host trees or rootstocks. The buds were forced into growth and eventually produced fruit. The fruit and tree characteristics resulting from such budding have proved to be identical to those of the original seedlings.

SUMMARY OF THE NEW VARIETY

The instant variety of peach tree is characterized by its general similarity to the Flavorcrest Peach Tree (unpatented), but has the important distinction of producing fruit which is more highly colored than that of the Flavorcrest and which ripens about 3 days earlier than such fruit. The surface of the fruit of the new variety is also smoother than that of the Flavorcrest in that the ventral suture of the fruit is seldom raised appreciably.

In comparison to the fruit of the Springcrest variety, the fruit of the instant variety ripens about three weeks later and is much larger in size.

The new peach tree is a large, regular and productive bearer of large, smoothly-shaped, nearly globular fruit. The fruit is uniform and symmetrical, highly colored, and has delicately-flavored, yellow flesh which is completely freestone.

BRIEF DESCRIPTION OF THE DRAWING

The accompanying drawing is a color photograph of three mature fruit of the subject variety with one of the fruit divided to show the flesh, pit and stone, together with a representative twig showing the characteristic leaves.

DETAILED DESCRIPTION

Referring more specifically to the pomological details of this new and distinct variety of peach tree, the following has been observed under the ecological conditions prevailing at the designated orchard at Fresno, Fresno County, Calif.

All color identifications are by reference to the Munsell Limit Color Cascade.

TREE

Size: Large.

Figure: Upright, spreading.

Productivity: Productive.

Regularity of bearing: Regular.

Trunk:

*Diameter in relation to length.*—Medium.

*Surface characteristics.*—Medium.

Branches:

*Size.*—Medium.

*Surface character.*—Medium.

*Color.*—Brown.

*Lenticels.*—Number — Medium; Size — Medium.

Leaves:

*Size.*—Medium.

*Length.*—16.55 cm.

*Width.*—3.81 cm.

*Shape.*—Lanceolate.

*Color.*—Medium green.

*Marginal form.*—Lanceolate, tip acutely pointed.

*Glandular characteristics.*—Crenate.

*Petiole.*—Length — Medium; Thickness — Medium.

*Stem glands.*—Number — Three (average); Arrangement — Alternate; Size — Small; Type — Globose; Color — Green.

Flower buds:

*Size.*—Medium.

*Shape.*—Plump.

*Surface.*—Pubescent.

*Other characteristics.*—Appressed.

Flowers:

*Date of bloom.*—March 10 (in 1982).

*Size.*—Large petals.

*Color.*—Pink.

FRUIT

Maturity: Approximately three days before Flavorcrest; June 26 in 1982.

Size:

*Uniformity.*—Uniform.

*Diameter.*—Axial — 6.76 cm.; Transverse in suture plane — 7.21 cm.; Transverse at right angles to suture plane — 7.11 cm.

Form:

*Uniformity.*—Uniform, globose.

*Symmetry.*—Symmetrical.

*Suture.*—A distinct but shallow line, sometimes depressed near base. Extends from base to near apex.

*Ventral surface.*—Rounded, slightly lipped toward base, lips nearly equal.

*Stem cavity.*—1.78 cm. deep; 2.6 cm. wide; rounded, elongated in suture plane.

*Base.*—Rounded.

*Apex.*—Slight, rounded.

*Pistil point.*—Apical.

*Stem.*—Length — Medium; Caliper — Medium.

Skin:

*Thickness.*—Medium.

*Texture.*—Medium.

*Tendency to crack.*—None.

*Color.*—(Blush) Plate 35-13; (Ground Color) Plate 29-4.

*Pubescence.*—Moderate, short.

Flesh:

*Color.*—Yellow, Plate 29-9; slight red streak. Surface of Pit Cavity — Yellow, tinged with red. Color of Pit Well — Plate 29-10.

*Amygdalin.*—Wanting.

*Juice.*—Abundant.

*Flavor.*—Delicate.

*Aroma.*—Slight.

*Texture.*—Medium, melting.

*Fibers.*—Tender.

*Ripening.*—Even.

*Eating quality.*—Excellent.

Stone:

*Adhesion.*—Free.

*Fibers.*—Few, adhere along dorsal and ventral edges.

*Size.*—Length — 3.16 cm.; Breadth — 2.35 cm.; Thickness — 1.87 cm.

*Form.*—Elliptical.

*Base.*—Slightly oblique.

*Sides.*—Equal.

*Ridges.*—Rounded, more numerous and deeper toward apex.

*Color.*—Variable, but within the range of 30-3 to 30-10.

*Splitting tendency.*—Slight.

Use: Commercial shipping; fresh market.

Keeping quality: Good.

Shipping quality: Good.

Although the new variety of peach tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of peach tree, what I claim as new and desire to secure by Letters Patent is:

1. A new and distinct variety of peach tree, substantially as illustrated and described, and which is characterized by its regular and productive bearing of large, yellow-fleshed and delicately-flavored fruit; and by its general resemblance to the Flavorcrest Peach Tree (unpatented), but from which it is distinguished by its fruit ripening about three days earlier and having a more highly red colored skin, and having a smoother exterior surface in that the ventral suture is seldom raised appreciably.

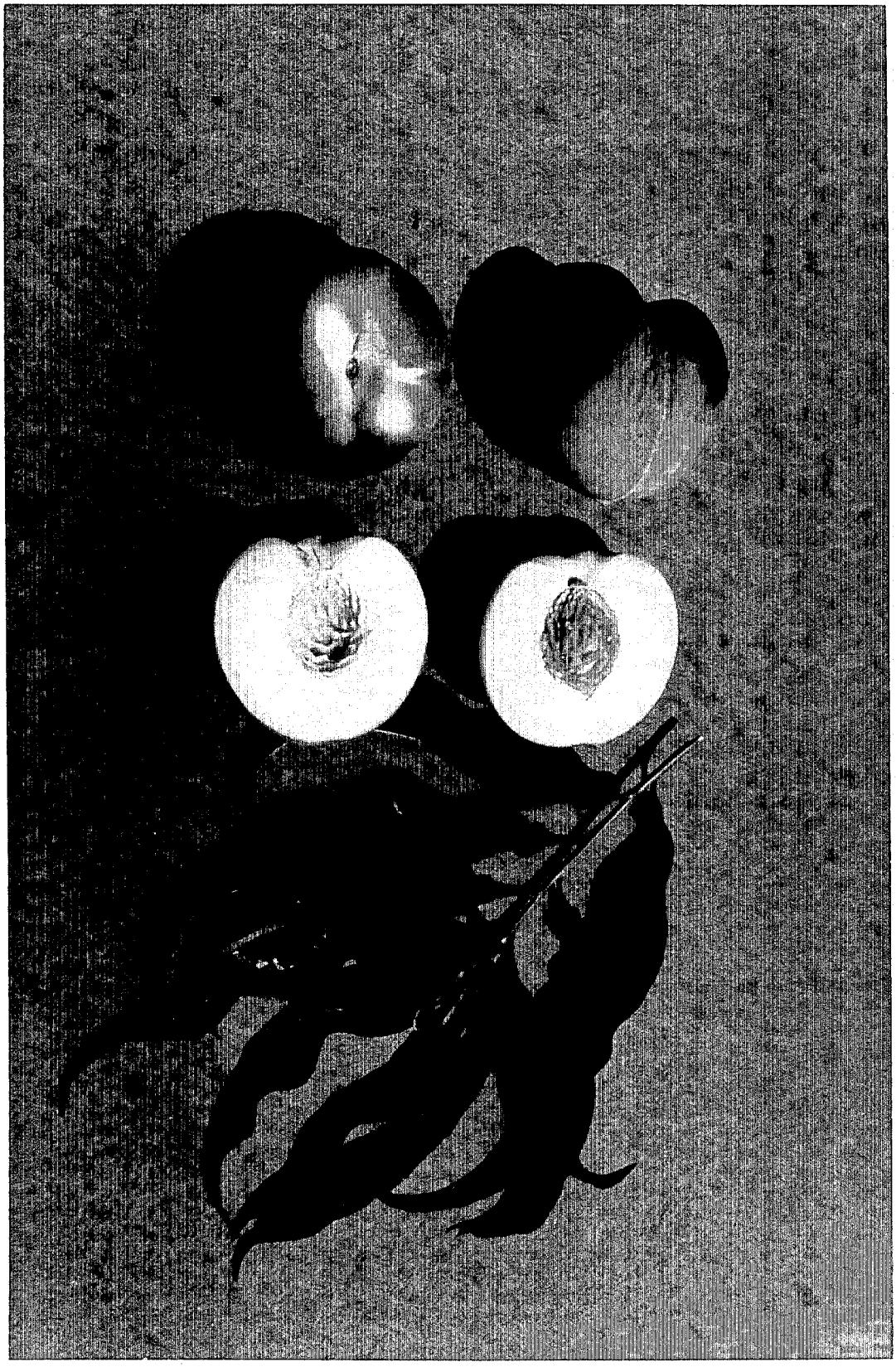

* * * * *